United States Patent
Karim et al.

(10) Patent No.: US 10,112,883 B2
(45) Date of Patent: Oct. 30, 2018

(54) PRODUCTION OF PRODUCTS FROM NATURAL RESOURCES

(71) Applicant: SAUDI BASIC INDUSTRIES CORPORATION, Riyadh (SA)

(72) Inventors: Khalid Karim, Riyadh (SA); Labeeb Chaudhary Ahmed, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/786,010

(22) PCT Filed: Apr. 22, 2014

(86) PCT No.: PCT/IB2014/001420
§ 371 (c)(1),
(2) Date: Oct. 21, 2015

(87) PCT Pub. No.: WO2014/174372
PCT Pub. Date: Oct. 30, 2014

(65) Prior Publication Data
US 2016/0096796 A1    Apr. 7, 2016

Related U.S. Application Data

(60) Provisional application No. 61/815,463, filed on Apr. 24, 2013.

(51) Int. Cl.
| | | |
|---|---|---|
| *C07C 51/225* | (2006.01) | |
| *C07C 51/215* | (2006.01) | |
| *B01J 27/057* | (2006.01) | |
| *B01J 27/187* | (2006.01) | |
| *B01J 23/889* | (2006.01) | |
| *C07C 1/04* | (2006.01) | |
| *C07C 51/25* | (2006.01) | |
| *B01J 37/03* | (2006.01) | |
| *B01J 27/051* | (2006.01) | |

(52) U.S. Cl.
CPC ......... *C07C 51/225* (2013.01); *B01J 23/8892* (2013.01); *B01J 27/0515* (2013.01); *B01J 27/0576* (2013.01); *B01J 27/187* (2013.01); *B01J 37/035* (2013.01); *C07C 1/0435* (2013.01); *C07C 1/0485* (2013.01); *C07C 51/215* (2013.01); *C07C 51/252* (2013.01); *C07C 2523/889* (2013.01); *C07C 2527/187* (2013.01)

(58) Field of Classification Search
CPC ... C07C 51/225; C07C 51/215; C07C 1/0485; C07C 1/0435; C07C 2527/187; C07C 2523/889; B01J 27/187; B01J 23/8892; B01J 27/0576
USPC ............................................. 562/512.2
See application file for complete search history.

(56) References Cited

U.S. PATENT DOCUMENTS

| | | | |
|---|---|---|---|
| 6,160,162 A | 12/2000 | Karim et al. | |
| 2008/0161602 A1 | 7/2008 | Wang et al. | |
| 2009/0264286 A1* | 10/2009 | Takeshima | .......... C01F 17/0043 502/325 |
| 2010/0261940 A1* | 10/2010 | Jun | .......... C07C 1/044 585/324 |
| 2011/0118365 A1 | 5/2011 | Steiner et al. | |

FOREIGN PATENT DOCUMENTS

| | | |
|---|---|---|
| CN | 86105974 A | 7/1987 |
| CN | 1326378 A | 12/2001 |
| CN | 101745403 A | 6/2010 |
| CN | 101868434 A | 10/2010 |
| CN | 102500425 A | 6/2012 |
| EP | 0187102 A1 | 7/1986 |
| EP | 0196732 A1 | 10/1986 |
| EP | 0216472 A1 | 4/1987 |
| FR | 2391978 A1 | 12/1978 |
| WO | WO-2000/029106 A1 | 5/2000 |
| WO | WO-2011/141374 A1 | 11/2011 |
| WO | WO-2012/084160 A1 | 6/2012 |

OTHER PUBLICATIONS

Das et al. Synthesis of light alkenes from syngas on silicalite-1 supported cobalt and cobalt-manganese catalysts. Applied Catalysis A: General 131 (1995) 335-345.*

(Continued)

*Primary Examiner* — Yih-Horng Shiao
(74) *Attorney, Agent, or Firm* — Ballard Spahr LLP

(57) ABSTRACT

The method disclosed herein relates to two stage catalytic processes for converting syngas to acetic acid, acrylic acid and/or propylene. More specifically, the method described and claimed herein relate to a method of producing acrylic acid and acetic acid comprising the steps of: a) providing a feedstream comprising syngas; b) contacting the feedstream with a first catalyst to produce a first product stream comprising $C_2$-$C_3$ olefins and/or $C_2$-$C_3$ paraffins; and c) contacting the first product stream with oxygen gas and a second catalyst, thereby producing a second product stream comprising acrylic acid and acetic acid, wherein there is no step for separating the components of the first product stream before the first product stream is contacted with the second catalyst.

19 Claims, No Drawings

(56) References Cited

OTHER PUBLICATIONS

International Search Report dated Jan. 5, 2015 by the International Searching Authority for International Patent Application No. PCT/IB2014/001420, which was filed on Apr. 22, 2014 and published as WO 2014/174372 on Oct. 30, 2014 (Inventor—KArim et al.; Applicant—Saudi Basic Industries Corp.; (6 pages).
Janardanarao, M., Direct Catalytic Conversion of Synthesis Gas to Lower Olefins, Ind Eng Chem Res, 29(9): 1735-53 (1990).

* cited by examiner though it is conceivable to make acrylic acid from methanol-based acetic acid via acetic acid and formaldehyde (from methanol), such a process is complicated and does not lend itself to easy commercial production.

PRODUCTION OF PRODUCTS FROM NATURAL RESOURCES

CROSS-REFERENCE TO RELATED APPLICATIONS

This Application is a U.S. National Phase Application of International Application No. PCT/IB2014/001420, filed Apr. 22, 2014, which claims the benefit of U.S. Provisional Application No. 61/815,463, filed on Apr. 24, 2013, which are both incorporated herein by reference in their entirety.

FIELD OF THE INVENTION

The disclosed methods relate to a process for converting syngas into useful products.

BACKGROUND

Syngas comprises hydrogen ($H_2$) and carbon monoxide (CO) and can be readily produced from either coal or methane (natural gas) by methods well known in the art and widely commercially practiced around the world. Syngas can also be produced from biomass, via a number of well-known processes.

The Fischer-Tropsch catalytic process for catalytically producing hydrocarbons from syngas was developed in the 1920's, and was used in South Africa for many years to produce gasoline range hydrocarbons as automotive fuels. Those catalysts typically comprised iron or cobalt supported on alumina or titania, and promoters, like rhenium, zirconium, manganese, and the like were sometimes used with cobalt catalysts, to improve various aspects of catalytic performance. The products were typically gasoline-range hydrocarbon liquids having six or more carbon atoms, along with heavier hydrocarbon products. More recently however, the Fischer-Tropsch process has been increasingly focused on and developed as methods for preparing the heavier hydrocarbons suitable for use as diesel fuels, and/or waxy hydrocarbon molecules suitable for conversion to clean, efficient lubricants.

A number of modern and well-known industrial processes also use syngas as a starting material for producing various oxygenated organic chemicals. For example, syngas can be readily and efficiently catalytically converted to methanol, then the methanol can be further efficiently reacted with carbon monoxide (separated from syngas) in the presence of soluble Rh/I or Ir/I catalysts to produce acetic acid, and both of these process steps are widely commercially practiced around the world.

Propane and propylene are also widely produced commercially, typically from oil, via a variety of processes commercially practiced in oil refineries. Propylene is particularly valuable for making a variety of high value downstream products, via known commercial processes, and commands a significantly higher price than propane. The vapor phase oxidation of propylene to acrylic acid with air or oxygen, over supported metal oxide catalysts is commercially practiced.

There are also some reports of direct catalytic oxidation of propane to acrylic acid. A highly selective propane to acrylic acid process could potentially be more economically attractive than a propylene-based process, because of the significant price difference between propane and propylene as starting materials.

Disclosed herein are methods related to a catalytic process that converts syngas to useful products.

SUMMARY OF THE INVENTION

Disclosed herein are methods of producing acrylic acid and acetic acid comprising the steps of:
a) providing a feedstream comprising syngas;
b) contacting the feedstream with a first catalyst to produce a first product stream comprising $C_2$-$C_3$ olefins and/or $C_2$-$C_3$ paraffins; and
c) contacting the first product stream with oxygen gas and a second catalyst, thereby producing a second product stream comprising acrylic acid and acetic acid,
wherein there is no step for separating the components of the first product stream before the first product stream is contacted with the second catalyst.

Additional advantages will be set forth in part in the description which follows, and in part will be obvious from the description, or may be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DETAILED DESCRIPTION

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds may not be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated herein and should be considered disclosed herein.

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. In some aspects (but not all) of the methods disclosed herein, recitation of the word "about" in connection with a particular disclosed value can mean ±10% of the particular disclosed value, unless an interpretation to the contrary is necessary or indicated.

References in the specification and concluding claims to "parts by weight" of a particular element or component in a composition or article, which denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Many of the catalyst compositions and/or catalyst components disclosed herein are described as containing a "metal" or "metals". Examples of such "metal" components include B, La, Mn, Co, Sb, Ti, Zr, Fe, Cs, Au, and Ce, Na, K, Mg, or Ca, and La, Te, Ge, Zn, Si, In, or W. It should be understood that references to such "metals" in this application does NOT imply a particular valence, chemical, or physical state of those elements, or that those elements are necessarily in a zero valent state, or metallic solid physical state or alloy (although they could be in such states), but rather that the term "metal" or "metals" can also be present in a compound with other elements or groups wherein the metal can be present in any energetically feasible positive oxidation state (i.e. cationic oxidation states). For example, a reference to potassium (K) as a metal could include bulk metallic potassium in a zero oxidation state, or dispersions or solutions of potassium metal, or also the cationic form $K^+$ of potassium, which may be present in either liquid or crystalline solutions with other elements.

The term "syngas is converted to" or the like terms refer to the conversion of syngas as a whole or the conversion of CO present in the syngas.

Some of the catalyst compositions described herein are in oxide form. It is well known that such oxides are reduced under the reaction conditions necessary to make the products disclosed herein. Therefore, the disclosed oxide forms are also inclusive of the reduced forms of the catalyst compositions present during the reactions disclosed herein.

1. Methods for Producing Acrylic Acid and Acetic Acid from Syngas

In some of many aspects, the inventions described and claimed herein relate to methods of producing acrylic acid and acetic acid comprising the steps of:

a) providing a feedstream comprising syngas;
b) contacting the feedstream with a first catalyst to produce a first product stream comprising $C_2$-$C_3$ olefins and/or $C_2$-$C_3$ paraffins; and
c) contacting the first product stream with oxygen gas and a second catalyst, thereby producing a second product stream comprising acrylic acid and acetic acid,
wherein there is no step for separating the components of the first product stream before the first product stream is contacted with the second catalyst.

In one aspect, step b can be performed in a first vessel and step c can be performed in a second vessel. In step b the feedstream of syngas react with a first catalyst to produce ethylene or propylene or both and in step c the total stream can react with a second catalyst to make carboxylic acid, acrylic acid, or acetic acid, or a mixture thereof.

2. Feedstreams Comprising Syngas

The feedstreams for the methods described herein comprise syngas, and optionally diluent gases. Syngas is a mixture of varying ratios of hydrogen ($H_2$) and carbon monoxide (CO) gases. Many methods for producing and/or providing syngas from feedstocks such a natural gas, coal, or waste streams or biomass, at almost any desired ratio of hydrogen to carbon monoxide, are well known to those of ordinary skill in the art. The commonly commercially practiced method for making syngas is via high temperature steam reforming of natural gas (i.e. $CH_4$, methane) according to the following equation:

$$CH_4 + H_2O \rightarrow CO + 3H_2$$

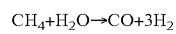

Many methods for altering the ratio of CO and $H_2$ in the syngas are known in the art, including numerous methods for partial or complete separation of CO and $H_2$, such as pressure swing absorption. Furthermore, in order to increase the amount of hydrogen in syngas, more steam can be added to the methane feed, and the water gas shift reaction can also be carried out on part of the CO produced:

$$CO + H_2O \rightarrow CO_2 + H_2$$

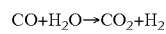

The hydrogen and carbon monoxide can be separated from the $CO_2$ produced, by pressure swing adsorption (PSA), amine scrubbing, and membrane reactors.

Syngas is also sometimes commercially produced by pyrolysis of coal to form incandescent coke, which is then treated with alternating blasts of steam and oxygen, a process well known in the art and commercially practiced at some facilities. Syngas can also be produced from biomass and/or waste streams via methods that are already known or are the subject of research and development.

A large range of molar ratios of hydrogen to carbon monoxide can be suitable for the gaseous feedstreams suitable for the practice of the methods described herein. Since high conversion of carbon monoxide to hydrocarbons by contact with the first catalyst is typically desired, feedstreams comprising at least equimolar ratios of hydrogen to carbon monoxide or higher are typically employed, i.e. feedstreams comprising syngas in molar ratios from 4:1 $H_2$/CO to 1:1 $H_2$/CO are typically employed. In some aspects, the ratios of hydrogen to carbon monoxide employed are from 3:1 $H_2$/CO to 2:1 $H_2$/CO. In another aspect, the ratios of hydrogen to carbon monoxide employed are from 2:1 $H_2$/CO to 1:1 $H_2$/CO Optionally, inert carriers or diluent gases, such as $N_2$, $CO_2$, water, or water vapor (often in the form of steam), and the like can be mixed with the syngas. In many aspects of the methods described herein, water/steam, which is a natural product of the conversion of syngas to hydrocarbons, can be a suitable carrier or diluent gas. The carrier or diluent gases can be present in any proportion as compared to syngas, but generally comprise less than 50, 40, 30, 20, 10, or 5 mole % of the feedstream.

3. Conversion of Syngas to Hydrocarbons Over a First Catalyst

The methods of producing acrylic acid and acetic acid described herein include a step of
b) contacting the feedstream with a first catalyst to produce a first product stream comprising $C_2$-$C_3$ olefins and/or $C_2$-$C_3$ paraffins;

The first catalyst used in the methods of the invention can be any Fischer Tropsch catalyst that converts the syngas in the feedstream to hydrocarbons, including $C_2$-$C_3$ olefins and/or $C_2$-$C_3$ paraffins, which are suitable for oxidation to acrylic acid and/or acetic acid. Many suitable Fischer Tropsch catalysts are known in the art, but in many aspects of the present methods, the first catalyst can selectively produce $C_2$-$C_3$ olefins and/or $C_2$-$C_3$ paraffins, at least compared to higher molecular weight hydrocarbons.

In many aspects, the catalysts are mixed metal oxides, wherein metal atoms or ions are situated in the spaces between a solid lattice formed by oxide anions. As is known to those of ordinary skill in the art, such mixed metal oxides are often non-stoichiometric solids, which can contain solid state point defects (such as vacancies or interstitial atoms or ions) that can cause variations in the overall stoichiometry of the composition without dramatically effecting the bulk structure of the material. As a result, such mixed metal oxide compounds cannot be completely and accurately described by single definite ratios of moles of their atomic constituents as can be done for most organic compounds, but rather can only be described in terms of ranges of molar ratios of their components. Accordingly, for convenience and the purposes of this disclosure, the compositions for the catalytically active but non-stoichiometric mixed metal oxide catalysts described herein are quoted in ranges of ratios of moles of the atoms as compared to the moles of other ions or atoms in the same composition, wherein the number of oxygen atoms in the mixed metal oxide composition, which is determined by the valency requirements of the other metallic elements in the composition, as well as other internal and external factors, cannot be precisely specified.

In one aspect, the first catalyst comprises a solid mixed metal oxide having the formula (I)

$$Co_a Mo_b S_c M_d O_f \qquad (I)$$

wherein a is 1;
wherein b is from 0.8 to 1.2;
wherein c is from 1 to 2;
wherein M comprises Zn, Ti, Zr, Ni, or a mixture thereof,
wherein d is from 0.000001 to 0.2; and
wherein f is a number determined by the valence requirements of the other elements present in the catalyst.

The $Co_a Mo_b S_c M_d O_f$ compositions described herein can be prepared by modifying $CoMoS_2$, as described herein below, or by other methods, then exposing the composition to syngas at elevated temperatures. Such exposure produces a reduced form of the catalyst composition. The introduction of metal atoms or ions "M" onto or into solid $CoMoS_2$ can occur during the synthesis of the modified solids as described elsewhere herein. Partial substitution of the sulfur atoms or ions with oxygen can occur during the synthetic procedures, or when the modified solid is contacted with syngas at elevated temperatures characteristic of the conversion of syngas to hydrocarbons.

The $Co_a Mo_b S_c M_d O_f$ catalyst compositions described herein can be non-stoichiometric solids, i.e. single phase solid materials whose composition cannot be represented by simple ratios of well-defined simple integers, because those solids probably contain solid state point defects (such as vacancies or interstitial atoms or ions) that can cause variations in the overall stoichiometry of the composition. Such phenomena are well known to those of ordinary skill in the arts related to solid inorganic materials, especially for transition metal oxides and sulfides. Accordingly, for convenience and the purposes of this disclosure, the composition of the potentially non-stoichiometric catalytically active solids described herein will be quoted in ratios of moles of the other atoms as compared to the moles of cobalt ions or atoms in the same composition, whatever the absolute concentration of cobalt present in the composition. Accordingly, for purposes of this disclosure, the value of "a" will be assumed to be 1 (one), regardless of the absolute concentration of cobalt in the catalyst composition, and the subscript numbers for the other elements representing the molar ratios that need not be integer ratios.

In the $Co_a Mo_b S_c M_d O_f$ catalyst compositions described herein, the molar ratio of molybdenum atoms to cobalt atoms, i.e. the value of "b" in the formulas for the composition, can be from 0.8 to 1.2, or from 0.9 to 1.1, varying somewhat on the presence and quantity of the additional transition metal atoms or ions "M". In one aspect, b can be 1.

During the synthesis of the $Co_a Mo_b S_c M_d O_f$ catalyst compositions described herein, the quantity of sulfur atoms or ions that were initially present in the "parent" solid $CoMoS_2$, can vary and/or change significantly, so that the molar coefficient "c" representing the relative quantity of sulfur in the final composition can range from 1 to 2, or from 1 to 1.5. In one aspect, c can be 1.

"M" can be a transition metal atom or ion comprises Zn, Ti, Zr, or Ni, or a mixture thereof, and can be present in molar ratios as compared to cobalt corresponding to a coefficient "d" from 0.0001 to 0.2, or from 0.001 to 0.01, or from 0.004 to 0.01. In one aspect, M can be Zn. In another aspect, M can be Ti. In yet another aspect, M can be Ni.

In the $Co_a Mo_b S_c M_d O_f$ catalyst compositions described herein, the molar ratio of oxygen atoms to cobalt atoms, i.e. the value of the coefficient "f" can be a number determined stochiometrically depending on the values of the other components in the catalyst composition. In one aspect, the value off can be any whole integer or decimal fraction between 0 and 10. In some aspects of the catalysts described herein, f is greater than zero. In some aspects of the catalysts described herein, f can be from 1 to 5.

In one aspect, f can be 0 (zero). Even though a suitable catalyst composition of these inventions may be prepared or loaded into a reactor in the form of a mixed oxide (i.e. f is initially greater than 0), contact with hot syngas, either before or during the catalytic conversion of syngas to hydrocarbons begins, may result in the "in-situ" reduction of the catalyst composition and/or partial or complete removal of oxygen from the solid catalyst composition, with the result that f can be decreased to zero or zero.

In one aspect, $Co_a Mo_b S_c M_d O_f$ can be optionally dispersed on or onto a catalyst support material, a binder, a filler, and/or a lubricant, and are shown herein below to be active for the selective conversion of syngas to $C_1$-$C_5$ hydrocarbons.

In another aspect, $Co_aMo_bS_cM_dO_f$ can be optionally dispersed on or onto a catalyst support material. Many such support materials are well known to those of ordinary skill in the art. They are typically catalytically inert, but typically provide physical support, strength and integrity to catalyst particles or pellets containing both the catalyst compositions and the support material, so that catalyst lifetimes are improved. Suitable support materials for the catalyst compositions described herein include clays, $Al_2O_3$, $SiO_2$, $TiO_2$, $CeO_2$, $AlPO_4$, $ZrO_2$, silicon-carbide, Molybdenum-carbide, alumino-silicates, zeolites, or molecular sieves, or a mixture thereof, or as separate components.

In yet another aspect, $Co_aMo_bS_cM_dO_f$ can be optionally dispersed on or onto a binder. Binders are typically inert inorganic oxides or clays that are resistant to the high temperature and other conditions of the processes described herein, but physically bind the zeolite particles together and/or increase their resistance to mechanical attrition. Often, the treated zeolite and the binder are mixed in a liquid solvent, then formed or molded into suitable shapes for catalyst pellets, such as pellets or tablets, then the liquid is removed and the catalyst pellet calcined, via methods known to those of ordinary skill in the art. The binders serve to provide physical integrity and mechanical strength to the catalyst particles. Suitable inorganic binders include alumina, silica, titania, zirconia, or magnesia, and suitable clays include montmorillonite or kaolin clays, or a mixture thereof. In some aspects, the catalyst binder is an alumina. In some aspects, the catalyst binder is silica. In some aspects, the catalyst binder is titania. In some aspects, the catalyst binder is zirconia. In some aspects, the catalyst binder is magnesia. In some aspects, the catalyst binder is clay.

In yet another aspect, $Co_aMo_bS_cM_dO_f$ can be optionally dispersed on or onto a filler. Suitable fillers include silicate or alumino-silicate clays, such as bentonite or montmorillonite clays.

In yet another aspect, $Co_aMo_bS_cM_dO_f$ can be optionally dispersed on or onto $K_2CO_3$.

In yet another aspect, $Co_aMo_bS_cM_dO_f$ can be optionally dispersed on or onto a lubricant. Lubricants are used to aid the formation of large composite particles or tablets from mixtures of the catalyst composition and supports and/or binders. Suitable lubricants include Sterotex, a powder comprising waxy hydrogenated vegetable oils available from ABITECH of Janesville Wis.

In another aspect of the methods for making acrylic acid and acetic acid, the first catalyst is a catalyst composition comprising cobalt, manganese, hydrophilic silica, and at least one element selected from the group of lanthanum, phosphorus, Fe, Zr and Zn, wherein the relative molar ratios of the elements comprised in said composition are represented by the formula (II)

$$Co_{a1}Mn_{b1}Si_{z1}X_{y1}M1_{d1}O_{f1}, \quad (II)$$

wherein a1 is 1;
wherein b1 is from 0.8 to 1.2;
wherein Si is in the form of a hydrophilic silica;
wherein z1 is from 0.1 to 1;
wherein X comprises La, P, Fe, Zr, Zn, or Cu, or a mixture thereof;
wherein y1 is greater than 0 to 0.005;
wherein M1 is one or more elements selected from the group consisting of alkali metal, alkaline earth metal and transition metal,
wherein d1 is 0 to 0.005;
wherein f1 is a number determined by the valence requirements of elements of the other elements present in the catalyst.

In one aspect, b1 is from 0.9 to 1.1. In another aspect, b1 is 1.

In one aspect, z1 is from 0.2 to 1. In another aspect, z1 is from 0.3 to 1. In yet another aspect, z1 is from 0.4 to 1. In yet another aspect, z1 is from 0.5 to 1. In yet another aspect, z1 is from 0.6 to 1. In yet another aspect, z1 is from 0.7 to 1. In yet another aspect, z1 is from 0.8 to 1. In yet another aspect, z1 is from 0.2 to 0.9. In yet another aspect, z1 is from 0.2 to 0.8. In yet another aspect, z1 is from 0.2 to 0.7. In yet another aspect, z1 is from 0.2 to 0.6. In yet another aspect, z1 is from 0.2 to 0.5. In yet another aspect, z1 is 0.2. In yet another aspect, z1 is 0.3. In yet another aspect, z1 is 0.4. In yet another aspect, z1 is 0.5. In yet another aspect, z1 is 0.6. In yet another aspect, z1 is 0.7. In yet another aspect, z1 is 0.8. In yet another aspect, z1 is 0.9. In yet another aspect, z1 is 1.

In one aspect, y1 is greater than 0 to 0.0001. In another aspect, y1 is greater than 0 to 0.00001. In yet another aspect, y1 is greater than 0 to 0.000001. In yet another aspect, y1 is greater than 0 to 0.001.

In one aspect, d1 is greater than 0 to 0.005. In another aspect, d1 is 0. In yet another aspect, d1 is greater than 0 to 0.001. In yet another aspect, d1 is greater than 0 to 0.0001. In yet another aspect, d1 is greater than 0 to 0.000001.

In one aspect, b1 is 1, z1 is from 0.8 to 1, y1 is greater than 0 to 0.000001, and d1 is greater than 0 to 0.000001.

In one aspect, M1 is an alkali metal. In another aspect, M1 is an alkaline earth metal. In yet another aspect, M1 is a transition metal.

In one aspect of the catalysts of Formula (II), M1 comprises sodium (Na), potassium (K), rubidium (Rb), cesium (Cs), magnesium (Mg), calcium (Ca), strontium (Sr), barium (Ba), titanium (Ti), zirconium (Zr), or copper (Cu), or a mixture thereof. In another aspect, M1 is Na. In yet another aspect M1 is K. In yet another aspect M1 is Rb. In yet another aspect M1 is Cs. In yet another aspect M1 is Mg. In yet another aspect M1 is Ca. In yet another aspect M1 is Ca. In yet another aspect M1 is Sr. In yet another aspect M1 is Ba. In yet another aspect M1 is Ti. In yet another aspect M1 is Zr. In yet another aspect M1 is Cu.

In one aspect of the catalysts of Formula (II), X is La and P. In another aspect, X is La. In yet another aspect, X is P. In yet another aspect of the catalysts of Formula (II), X is one element and is Fe, Zr, or Zn. In yet another aspect, X is Fe. In yet another aspect, X is Zr. In yet another aspect, X is Zn.

In one aspect, at least one of M1 and X is not Zr.

In some aspects of the catalysts of Formula (II), the hydrophilic silica has a specific surface area from 200 $m^2/g$ to 400 $m^2/g$. In some aspects of the catalysts of Formula (II), the hydrophilic silica has a pH of 3.7-4.7.

In one aspect, $Co_{a1}Mn_{b1}Si_{z1}X_{y1}M1_{d1}O_n$ can be optionally dispersed on or onto a catalyst support material, a binder, a filler, and/or a lubricant, and are shown herein below to be active for the selective conversion of syngas to $C_1$-$C_5$ hydrocarbons.

In another aspect, $Co_{a1}Mn_{b1}Si_{z1}X_{y1}M1_{d1}O_n$ can be optionally dispersed on or onto a catalyst support material. Many such support materials are well known to those of ordinary skill in the art. They are typically catalytically inert, but typically provide physical support, strength and integrity to catalyst particles or pellets containing both the catalyst compositions and the support material, so that catalyst lifetimes are improved. Suitable support materials for the catalyst compositions described herein include clays, $Al_2O_3$, $SiO_2$, $TiO_2$, $CeO_2$, $AlPO_4$, $ZrO_2$, silicon-carbide, Molybdenum-carbide, alumino-silicates, zeolites, or molecular sieves, or a mixture thereof, or as separate components.

In yet another aspect, $Co_{a1}Mn_{b1}Si_{z1}X_{y1}M1_{d1}O_n$ can be optionally dispersed on or onto a binder. Binders are typically inert inorganic oxides or clays that are resistant to the high temperature and other conditions of the processes described herein, but physically bind the zeolite particles together and/or increase their resistance to mechanical attrition. Often, the treated zeolite and the binder are mixed in a liquid solvent, then formed or molded into suitable shapes for catalyst pellets, such as pellets or tablets, then the liquid is removed and the catalyst pellet calcined, via methods known to those of ordinary skill in the art. The binders serve to provide physical integrity and mechanical strength to the catalyst particles. Suitable inorganic binders include alumina, silica, titania, zirconia, or magnesia, and suitable clays including montmorillonite and kaolin clays, and a mixture thereof. In some aspects, the catalyst binder is an alumina. In some aspects, the catalyst binder is silica. In some aspects, the catalyst binder is titania. In some aspects, the catalyst binder is zirconia. In some aspects, the catalyst binder is magnesia. In some aspects, the catalyst binder is clay.

In yet another aspect, $Co_{a1}Mn_{b1}Si_{z1}X_{y1}M1_{d1}O_n$ can be optionally dispersed on or onto a filler. Suitable fillers include silicate or alumino-silicate clays, such as bentonite or montmorillonite clays.

In yet another aspect, $Co_{a1}Mn_{b1}Si_{z1}X_{y1}M1_{d1}O_n$ can be optionally dispersed on or onto a lubricant. Lubricants are used to aid the formation of large composite particles or tablets from mixtures of the catalyst composition and supports and/or binders.

In some aspects of the methods for making acrylic acid and acetic acid, the first catalyst comprises a mixed metal oxide represented by the formula (III)

$$Co_{a2}Mn_{b2}La_{z2}P_{y2}M2_{d2}O_{f2}, \tag{III}$$

wherein a2 is 1;
wherein b2 is from 0.8 to 1.2;
wherein z2 is greater than 0 to 0.5;
wherein y2 is greater than 0 to 0.5;
wherein M2 comprises an alkali metal, alkaline earth metal, or transition metal, or a mixture thereof,
wherein d2 is greater than 0 to 0.5; and
wherein f2 is a number determined by the valence requirements of elements of the other elements present in the catalyst as well as other internal and external factors, and can include zero.

In one aspect, b2 is from 0.9 to 1.1. In another aspect, b2 is 1.

In one aspect, z2 is greater than 0 to 0.4. In another aspect, z2 is greater than 0 to 0.3. In yet another aspect, z2 is greater than 0 to 0.2. In yet another aspect, z2 is greater than 0 to 0.1. In yet another aspect, z2 is 0.1 to 0.5. In yet another aspect, z2 is from 0.2 to 0.5. In yet another aspect, z2 is from 0.3 to 0.5. In yet another aspect, z2 is from 0.4 to 0.5.

In one aspect, y2 is greater than 0 to 0.4. In another aspect, y2 is greater than 0 to 0.3. In yet another aspect, y2 is greater than 0 to 0.2. In yet another aspect, y2 is greater than 0 to 0.1. In yet another aspect, y2 is from 0.1 to 0.5. In yet another aspect, from y2 is 0.2 to 0.5. In yet another aspect, from y2 is 0.3 to 0.5. In yet another aspect, y2 is from 0.4 to 0.5.

In one aspect, d2 is greater than 0 to 0.4. In another aspect, d2 is greater than 0 to 0.3. In yet another aspect, d2 is greater than 0 to 0.2. In yet another aspect, d2 is greater than 0 to 0.1. In yet another aspect, d2 is from 0.1 to 0.5. In yet another aspect, d2 is from 0.2 to 0.5. In yet another aspect, d2 is from 0.3 to 0.5. In yet another aspect, d2 is from 0.4 to 0.5.

In one aspect, b2 is 1, z2 is greater than 0 to 0.1, y2 is greater than 0 to 0.1, and d2 is greater than 0 to 0.1.

In one aspect, M2 is an alkali metal. In another aspect, M2 is an alkaline earth metal. In yet another aspect, M2 is a transition metal.

In one aspect of the catalysts of Formula (III), M2 comprises sodium (Na), potassium (K), rubidium (Rb), cesium (Cs), magnesium (Mg), calcium (Ca), strontium (Sr), barium (Ba), titanium (Ti), or zirconium (Zr), or a mixture thereof. In another aspect, M2 is Na. In yet another aspect M2 is K. In yet another aspect M2 is Rb. In yet another aspect M2 is Cs. In yet another aspect M2 is Mg. In yet another aspect M2 is Ca. In yet another aspect M2 is Ca. In yet another aspect M2 is Sr. In yet another aspect M2 is Ba. In yet another aspect M2 is Ti. In yet another aspect M2 is Zr.

In yet another aspect, $Co_{a2}Mn_{b2}La_{z2}P_{y2}M2_{d2}O_{f2}$ can be optionally dispersed on or onto a binder. Binders are typically inert inorganic oxides or clays that are resistant to the high temperature and other conditions of the processes described herein, but physically bind the zeolite particles together and/or increase their resistance to mechanical attrition. Often, the treated zeolite and the binder are mixed in a liquid solvent, then formed or molded into suitable shapes for catalyst pellets, such as pellets or tablets, then the liquid is removed and the catalyst pellet calcined, via methods known to those of ordinary skill in the art. The binders serve to provide physical integrity and mechanical strength to the catalyst particles. Suitable inorganic binders include alumina, silica, titania, zirconia, or magnesia, and suitable clays including montmorillonite and kaolin clays, and a mixture thereof. In some aspects, the catalyst binder is an alumina. In some aspects, the catalyst binder is silica. In some aspects, the catalyst binder is titania. In some aspects, the catalyst binder is zirconia. In some aspects, the catalyst binder is magnesia. In some aspects, the catalyst binder is clay.

In yet another aspect, $Co_{a2}Mn_{b2}La_{z2}P_{y2}M2_{d2}O_{f2}$ can be optionally dispersed on or onto a filler. Suitable fillers include silicate or alumino-silicate clays, such as bentonite or montmorillonite clays.

In yet another aspect, $Co_{a2}Mn_{b2}La_{z2}P_{y2}M2_{d2}O_{f2}$ can be optionally dispersed on or onto a lubricant. Lubricants are used to aid the formation of large composite particles or tablets from mixtures of the catalyst composition and supports and/or binders.

The feedstream comprising the syngas is typically forced to flow through reactors comprising the first catalyst, wherein the reactors are designed to retain the first catalyst against the vapor phase flow of syngas, at temperatures sufficient to maintain most of the hydrocarbon products of the catalytic reactions in the vapor phase at the selected operating pressures. The catalyst particles can be packed into a fixed bed, or dispersed in a fluidized bed, or in other suitable arrangements known to those of ordinary skill in the art.

In one aspect of the methods of the reaction, the feedstream comprising syngas is contacted with the first catalyst at a temperature of at least 200° C., or at least 300° C., and at a temperature below 400° C. or from a temperature of 200° C. to 350° C.

In one aspect, the syngas is contacted with the catalyst compositions at a pressure of at least 5 bar, or at least, 10 bar, or at least 15 bar, or at least 25 bar, or at least 50 bar, or at least 75 bar, and less than 200 bar, or less than 100 bar. In many aspects of the methods of the reaction, the syngas is contacted with the catalyst compositions at a pressure from 5 bar to 100 bar.

In one aspect of the methods of the reaction, the syngas is contacted with the first catalyst at such a rate and/or in such a way as to produce relatively high conversions of the syngas and/or high conversions of carbon monoxide. In another aspect of the methods, at least 40%, at least 50%, at least 60%, at least 70%, or at least 80%, or at least 90%, or at least 95%, or at least 95% of the CO in syngas is converted to hydrocarbon materials. In another aspect of the methods, less than 25%, or less than 20% of the carbon monoxide fed to the reactors is converted to $CO_2$.

In one aspect, the first product stream comprises at least 30, 40, or 50 mole % $C_2$-$C_3$ olefins and/or $C_2$-$C_3$ paraffins. In another aspect, the first product stream does not comprise alcohols, such as $C_1$-$C_5$ alcohols.

4. Catalytic Processes for Converting the First Product Stream to Acrylic Acid and Acetic Acid The methods of producing acrylic acid and acetic acid described herein include a step of:

c) contacting the first product stream with oxygen gas and a second catalyst, thereby producing a second product stream comprising acrylic acid and acetic acid, wherein there is no step for separating the components of the first product stream before the first product stream is contacted with the second catalyst.

It is understood that the term "oxygen gas" can be pure oxygen or oxygen mixed with other gases, such as, for example, nitrogen and noble gases. Thus, the term "oxygen gas" includes air.

After the feedstream comprising syngas has contacted the first catalyst, a first product stream is produced that comprises any of the optional carriers or diluents from the feedstream, any residual unconverted syngas, and hydrocarbon vapors that comprise $C_2$-$C_3$ olefins and/or $C_2$-$C_3$ paraffins. This product stream is then mixed with an oxygen ($O_2$) containing gas (derived from air or any other suitable source) and any additional carrier or diluent gases, (such as $N_2$, $CO_2$, and water vapor or steam), then contacted with a second catalyst that is suitable for oxidizing the hydrocarbons (including $C_2$-$C_3$ olefins and/or $C_2$-$C_3$ paraffins) to produce a second product stream comprising acrylic acid and acetic acid. It is to be understood however that in the methods described herein, although oxygen and/or optional diluent gases may be added to first product stream before the resulting mixture is contacted with the second catalysts, and that mechanical equipment such as heat exchangers, compressors, etc may operate on the first product stream before it is contacted with the second catalyst, there is no step for separating the components of the first product stream before the first product stream, oxygen, and any carrier or diluent gases are contacted with the second catalyst.

Oxygen is typically added to the first product stream at a ratio of 0.01 to 25.0 mole % of molecular oxygen per mole of propane plus ethane, so as to enable the production of acrylic acid and/or acetic acid.

Suitable additional carriers or diluent gases to be added to the first product stream include $N_2$, $CO_2$, water vapor and/or steam. Water vapor or steam can be a desirable reaction diluent and act as a heat moderator for the second catalytic reaction. It can also act as a desorption accelerator of the reaction product in the vapor phase oxidation reaction.

Any of a number of catalysts may be employed as a second catalyst for the oxidation of the hydrocarbons in the first product stream, including the $C_2$-$C_3$ paraffins ethane and propane to acrylic acid and/or acetic acid. An example of suitable second catalysts include the catalysts described in WO 2000/029106, which is hereby incorporated by reference herein in its entirety, for its description of catalysts of formula (IV),

$$Mo_{a3}V_{b3}Ga_{c3}Pd_{d3}Nb_{e3}Z_{f3}, \quad (IV)$$

wherein a3 is 1,
wherein b3 is from 0.01 to 0.9,
wherein c3 is greater than 0 to 0.2,
wherein d3 is from 0.0000001 to 0.2,
wherein e3 is greater than 0 to 0.2,
wherein Z comprises La, Te, Ge, Zn, Si, In, or W, or a mixture thereof, and
wherein f3 is greater than 0 to 0.5.

The numerical values of a3, b3, c3, d3, e3 and f3 in formula (IV) represent the relative molar ratios of the elements Mo, V, Ga, Pd, Nb and X, respectively, in the catalyst. In one aspect, the elements are present in combination with oxygen in the form of various oxides, so as to have an overall formula (IVa)

$$Mo_{a3}V_{b3}Ga_{e3}Pd_{d3}Nb_{e3}X_{f3}O_{y3}, \quad (IVa)$$

wherein y3 is a number determined by the valence requirements of the other elements in the catalyst composition.

Such catalysts of formula (IV) and/or (Iva) can be prepared by the methods disclosed in WO 2000/029106.

In one aspect, b3 is from 0.01 to 0.8. In another aspect, b3 is from 0.01 to 0.7. In yet another aspect, b3 is from 0.01 to 0.6. In yet another aspect, b3 is from 0.01 to 0.5. In yet another aspect, b3 is from 0.01 to 0.4. In yet another aspect, b3 is from 0.01 to 0.2. In yet another aspect, b3 is from 0.01 to 0.1. In yet another aspect, z1 is from b3 is from 0.05 to 0.9. In yet another aspect, b3 is from 0.1 to 0.9. In yet another aspect, b3 is from 0.2 to 0.9. In yet another aspect, b3 is from 0.3 to 0.9. In yet another aspect, b3 is from 0.4 to 0.9. In yet another aspect, b3 is from 0.5 to 0.9. In yet another aspect, b3 is from 0.6 to 0.9. In yet another aspect, b3 is from 0.7 to 0.9.

In one aspect, c3 is greater than 0 to 0.1. In another aspect, c3 is greater than 0 to 0.05. In yet another aspect, c3 is greater than 0 to 0.01. In yet another aspect, c3 is greater than 0 to 0.001. In yet another aspect, c3 is greater than 0 to 0.0001. In yet another aspect, c3 is 0.05 to 0.2. In yet another aspect, c3 is 0.1 to 0.2

In one aspect, d3 is from 0.0000001 to 0.1. In another aspect, c3 d3 is from 0.0000001 to 0.05. In yet another aspect, d3 is from 0.0000001 to 0.01. In yet another aspect, d3 is from 0.0000001 to 0.001. In yet another aspect, d3 is from 0.0000001 to 0.0001. In yet another aspect, d3 is from 0.05 to 0.2. In yet another aspect, d3 is from 0.1 to 0.2.

In one aspect, e3 is greater than 0 to 0.1. In another aspect, e3 is greater than 0 to 0.05. In yet another aspect, e3 is greater than 0 to 0.01. In yet another aspect, e3 is greater than 0 to 0.001. In yet another aspect, e3 is greater than 0 to 0.0001. In yet another aspect, e3 is 0.05 to 0.2. In yet another aspect, e3 is 0.1 to 0.2.

In one aspect, f3 is greater than 0 to 0.4. In another aspect, f3 is greater than 0 to 0.3. In yet another aspect, f3 is greater than 0 to 0.2. In yet another aspect, f3 is greater than 0 to 0.1. In yet another aspect, f3 is 0.1 to 0.5. In yet another aspect, f3 is 0.2 to 0.5. In yet another aspect, f3 is 0.3 to 0.5. In yet another aspect, f3 is 0.4 to 0.5.

In one aspect, b3 is from 0.01 to 0.4, c3 is greater than 0 to 0.0001, d3 is from 0.0000001 to 0.0001, e3 is 0.1 to 0.2, and f3 is 0.2 to 0.5.

In one aspect, Z comprises Te. In another aspect, Z comprises La. In yet another aspect, Z comprises Ge. In yet another aspect, Z comprises Zn, In yet another aspect, Z comprises Si. In yet another aspect, Z comprises In. In yet another aspect, Z comprises W.

The second catalyst may also comprise a microporous or mesoporous support material, or a neutral or oxidative support material, such as for example $Al_2O_3$, $SiO_2$, $CeO_2$, $TiO_2$, $ZrO_2$, acetate-$SiO_2$, low surface area $TiO_2$, high surface area $TiO_2$, acetate-$Al_2O_3$, acetate-$ZrO_2$, acetate-$CeO_2$, $AlPO_4$, SiC, silicon-carbide, Mo-carbide, aluminum-silicate, zeolites, or molecular sieves, or a mixture thereof.

The support material for the second catalyst may also comprise additional optional components $M_s$ and $X_s$, wherein $M_s$ is a metal comprising B, La, Mn, Sb, Ti, Zr, La, Fe, Cs, Au, or Ce, or a mixture thereof; and wherein $X_s$ is optionally present and is an alkaline metal comprising Na, K, Mg, or Ca, or a mixture thereof. In some aspects, $M_s$ can be La, Zr, Ce, or Cs, or a mixture thereof. In some aspects, $M_s$ is La. In many aspects, the $M_s$ components are dispersed or nano-dispersed over the support material.

In many aspects, the second catalyst has a particle diameter size of 20 μm to 500 μm. In many aspects, the second catalyst is stable at least 600° C.

In many aspects, the contact between the first product stream and the catalyst occurs in a second reactor vessel. The reaction zone employed for the second contacting step generally has a pressure of from 1 to 50 bar, or from 1 to 30 bar; and a temperature from 150° C. to 450° C., preferably from 200° C. to 300° C.; at a contact time between the first product stream and the second catalyst from 0.01 second to 100 seconds, or from 0.1 second to 10 seconds; and a space hourly velocity from 50 to 50,000 $h^{-1}$, or from 100 to 10,000 $h^{-1}$, and from 200 to 3,000 $h^{-1}$.

After the contact between the first product stream, oxygen, and second catalyst produces a second product stream comprising acrylic acid and acetic acid, a step of separating the acrylic acid and acetic acid from each other and all other components is often carried out. Many methods for such separations are known in the art, including distillation, crystallizations, etc.

5. Products

In one aspect, at least 10% by weight of the syngas is converted to a first product stream comprising $C_2$-$C_3$ olefins and/or $C_2$-$C_3$ paraffins. In another aspect, at least 20% by weight of the syngas is converted to a first product stream comprising $C_2$-$C_3$ olefins and/or $C_2$-$C_3$ paraffins. In yet another aspect, at least 30% by weight of the syngas is converted a first product stream comprising $C_2$-$C_3$ olefins and/or $C_2$-$C_3$ paraffins. In yet another aspect, at least 40% by weight of the syngas is converted to a first product stream comprising $C_2$-$C_3$ olefins and/or $C_2$-$C_3$ paraffins. In yet another aspect, at least 50% by weight of the syngas is converted to a first product stream comprising $C_2$-$C_3$ olefins and/or $C_2$-$C_3$ paraffins. In yet another aspect, at least 60% by weight of the syngas is converted to a first product stream comprising $C_2$-$C_3$ olefins and/or $C_2$-$C_3$ paraffins. In yet another aspect, at least 70% by weight of the syngas is converted to a first product stream comprising $C_2$-$C_3$ olefins and/or $C_2$-$C_3$ paraffins. In yet another aspect, at least 80% by weight of the syngas is converted to a first product stream comprising $C_2$-$C_3$ olefins and/or $C_2$-$C_3$ paraffins. In yet another aspect, at least 90% by weight of the syngas is converted to a first product stream comprising $C_2$-$C_3$ olefins and/or $C_2$-$C_3$ paraffins. In yet another aspect, at least 95% by weight of the syngas is converted to a first product stream comprising $C_2$-$C_3$ olefins and/or $C_2$-$C_3$ paraffins. In yet another aspect, at least 99% by weight of the syngas is converted to a first product stream comprising $C_2$-$C_3$ olefins and/or $C_2$-$C_3$ paraffins.

In one aspect, at least 10% by weight of the syngas is converted to acrylic acid and/or acetic acid. In another aspect, at least 20% by weight of the syngas is converted to acrylic acid and/or acetic acid. In yet another aspect, at least 30% by weight of the syngas is converted to acrylic acid and/or acetic acid. In yet another aspect, at least 40% by weight of the syngas is converted to acrylic acid and/or acetic acid. In yet another aspect, at least 50% by weight of the syngas is converted to acrylic acid and/or acetic acid. In yet another aspect, at least 60% by weight of the syngas is converted to acrylic acid and/or acetic acid. In yet another aspect, at least 70% by weight of the syngas is converted to acrylic acid and/or acetic acid. In yet another aspect, at least 80% by weight of the syngas is converted to acrylic acid and/or acetic acid. In yet another aspect, at least 90% by weight of the syngas is converted to acrylic acid and/or acetic acid. In yet another aspect, at least 95% by weight of the syngas is converted to acrylic acid and/or acetic acid. In yet another aspect, at least 99% by weight of the syngas is converted to acrylic acid and/or acetic acid.

6. Aspects of the Disclosed Methods

Aspect 1: A method of producing acrylic acid and acetic acid comprising the steps of:
 a) providing a feedstream comprising syngas;
 b) contacting the feedstream with a first catalyst to produce a first product stream comprising $C_2$-$C_3$ olefins and/or $C_2$-$C_3$ paraffins; and
 c) contacting the first product stream with oxygen gas and a second catalyst, thereby producing a second product stream comprising acrylic acid and acetic acid,
 wherein there is no step for separating the components of the first product stream before the first product stream is contacted with the second catalyst.

Aspect 2: The method of aspect 1, wherein the method further comprises separating the acetic acid and the acrylic acid.

Aspect 3: The method of aspects 1 or 2, wherein the first catalyst is a catalyst composition comprising cobalt; manganese; hydrophilic silica; and at least one element comprising lanthanum, phosphorus, Fe, Zr, or Zn, wherein the relative molar ratios of the elements comprised in said composition are represented by the formula

wherein a1 is 1;
wherein b1 is from 0.8 to 1.2;
wherein Si is in the form of a hydrophilic silica;
wherein z1 is from 0.1 to 1;
wherein X is comprises La, P, Fe, Zr, or Zn, or a mixture thereof;
wherein y1 is greater than 0 to 0.005;
wherein M1 is one or more elements selected from the group consisting of alkali metal, alkaline earth metal and transition metal,
wherein d1 is 0 to 0.005;

wherein f1 is a number determined by the valence requirements of elements of the other elements present in the catalyst.

Aspect 4: The method of aspect 3, wherein M1 comprises Na, K, Rb, Cs, Mg, Ca, Sr, Ba, Ti, or Zr, or a mixture thereof.

Aspect 5: The method of aspects 3 or 4, wherein X is La and P.

Aspect 6: The method of aspects 3 or 4, wherein X is one element and is Fe, Zr, or Zn.

Aspect 7: The method of any one of aspects 3-6, wherein the hydrophilic silica has a specific surface area from 200 m²/g to 400 m²/g.

Aspect 8: The method of any one of aspects 3-7, wherein the hydrophilic silica has a pH of 3.7-4.7.

Aspect 9: The method of aspects 1 or 2, wherein the first catalyst comprises a mixed metal oxide represented by the formula

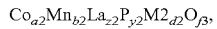

$Co_{a2}Mn_{b2}La_{z2}P_{y2}M2_{d2}O_{f2}$, wherein a2 is 1;
wherein b2 is from 0.8 to 1.2;
wherein z2 is greater than 0 to 0.5;
wherein y2 is greater than 0 to 0.5;
wherein M2 comprises an alkali metal, alkaline earth metal, or transition metal, or a mixture thereof,
wherein d2 is greater than 0 to 0.5; and
wherein f2 is a number determined by the valence requirements of elements of the other elements present in the catalyst.

Aspect 10: The method of aspect 9, wherein the M2 comprises Na, K, Rb, Cs, Mg, Ca, Sr, Ba, Ti, or Zr, or a mixture thereof.

Aspect 11: The method of aspects 9 or 10, wherein the first catalyst comprises a binder.

Aspect 12: The method of aspect 11, wherein the binder is selected from the group consisting of silica, alumina, titania, zirconia, carbon and zeolite.

Aspect 13: The method of aspects 1 or 2, wherein the first catalyst comprises $Co_aMo_bS_cM_dK_eO_f$,
wherein a is 1;
wherein b is from 0.8 to 1.2;
wherein c is from 1 to 3;
wherein M comprises Zn, Ti, Zr, or Ni, or a mixture thereof,
wherein d is from 0.000001 to 0.2;
wherein e is 0 to 0.2; and
wherein f is a number determined by the valence requirements of elements of the other elements present in the catalyst.

Aspect 14: The method of aspect 13, wherein M comprises Zn.

Aspect 15: The method of aspect 13, wherein M comprises Ti.

Aspect 16: The method of aspect 13, wherein M comprises Zr.

Aspect 17: The method of aspect 13, wherein M comprises Ni.

Aspect 18: The method of any one of aspects 13-17, wherein d is from 0.001 to 0.01.

Aspect 19: The method of any one of aspects 13-17, wherein d is from 0.004 to 0.01.

Aspect 20: The method of any one of aspects 13-19, wherein e is greater than 0.

Aspect 21: The method of any one of aspects 13-20, wherein e is 0.

Aspect 22: The method of any one of aspects 13-21, wherein the first catalyst composition further comprises a support material.

Aspect 23: The method of aspect 22, wherein the support material comprises $Al_2O_3$, $SiO_2$, $TiO_2$, $CeO_2$, $AlPO_4$, $ZrO_2$, SiC, silicon-carbide, Mo-carbide, aluminumsilicate, a zeolite, or a molecular sieve, or a mixture thereof.

Aspect 24: The method of any one of aspects 1-23, wherein the first catalyst converts syngas to $C_2$-$C_3$ olefins and/or $C_2$-$C_3$ paraffins.

Aspect 25: The method of any one of aspects 1-24, wherein the first product stream comprises at least 30% $C_2$-$C_3$ olefins and/or $C_2$-$C_3$ paraffins.

Aspect 26: The method of any one of aspects 1-24, wherein the first product stream comprises at least 40% $C_2$-$C_3$ olefins and/or $C_2$-$C_3$ paraffins.

Aspect 27: The method of any one of aspects 1-24, wherein the first product stream comprises at least 50% $C_2$-$C_3$ olefins and/or $C_2$-$C_3$ paraffins.

Aspect 28: The method of any one of aspects 1-27, wherein the first product stream does not comprise $C_1$-$C_5$ alcohols.

Aspect 29: The method of any one of aspects 1-28, wherein the second catalyst comprises

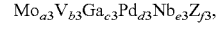

$Mo_{a3}V_{b3}Ga_{c3}Pd_{d3}Nb_{e3}Z_{f3}$, wherein a3 is 1,
wherein b3 is from 0.01 to 0.9,
wherein c3 is greater than 0 to 0.2,
wherein d3 is from 0.0000001 to 0.2,
wherein e3 is greater than 0 to 0.2,
wherein Z comprises La, Te, Ge, Zn, Si, In, or W, or a mixture thereof,
wherein f3 is greater than 0 to 0.5.

Aspect 30: The method of aspect 29, wherein Z comprises Te.

Aspect 31: The method of aspects 29 or 30, wherein the second catalyst comprises a support material.

Aspect 32: The method of aspect 31, wherein the support material comprises $Al_2O_3$, $SiO_2$, $CeO_2$, $TiO_2$, $ZrO_2$, acetate-$SiO_2$, low surface area $TiO_2$, high surface area $TiO_2$, acetate-$Al_2O_3$, acetate-ZrO2, acetate-$CeO_2$, $AlPO_4$, SiC, silicon-carbide, Mo-carbide, aluminumsilicate, a zeolite, or a molecular sieve, or a mixture thereof.

Aspect 33: The method of aspects 31 or 32, wherein the support material is neutral or oxidative.

Aspect 34: The method of any one of aspects 31-33, wherein the support material is a microporous or mesoporous support material.

Aspect 35: The method of any one of aspects 31-34, wherein the support material comprises additional components $M_s$ and $X_s$,
wherein $M_s$ is a metal comprising B, La, Mn, Sb, Ti, Zr, La, Fe, Cs, Au, or Ce; and
wherein $X_s$ is optionally present and is an alkaline metal comprising Na, K, Mg, or Ca.

Aspect 36: The method of aspect 35, wherein the support material comprises $Al_2O_3$, $SiO_2$, $TiO_2$, $CeO_2$, $AlPO_4$, $ZrO_2$, SiC, Mo-carbide, aluminumsilicate, a zeolite, or a molecular sieve, or a mixture thereof.

Aspect 37: The method of aspects 35 or 36, wherein $M_s$ is dispersed over the support material.

Aspect 38: The method of aspects 35 or 36, wherein $M_s$ is nano-dispersed over the support material.

Aspect 39: The method of any one of aspects 35-38, wherein the support material is a microporous or mesoporous material.

Aspect 40: The method of any one of aspects 35-39, wherein the second catalyst has a particle diameter size of 20 μm to 500 μm.

Aspect 41: The method of any one of aspects 35-40, wherein $M_s$ comprises La, Zr, Ce, or Cs.

Aspect 42: The method of any one of aspects 35-40, wherein $M_s$ comprises La.

Aspect 43: The method of any one of aspects 29-42, wherein the second catalyst is stable at at least 600° C.

Aspect 44: The method of any one of aspects 29-42, wherein the second catalyst is at least 20% more effective in oxidizing propane to acrylic acid than a base second catalyst.

Aspect 45: The method of any one of aspects 1-42, wherein the syngas is produced from coal, biomass, or natural gas.

Aspect 46: The method of any one of aspects 1-42, wherein the method further comprises providing coal, biomass, or natural gas prior to providing the syngas.

Aspect 47: The method of any one of aspects 1-42, wherein providing syngas comprises producing syngas from coal, biomass, or natural gas.

Aspect 48: The method of any one of aspects 1-47, wherein step b) is performed in a first vessel and step c) is performed in a second vessel.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Reaction products described blow can be analyzed on-line by gas chromatography. Oxygen, argon and carbon monoxide can be analyzed using a 2.5 mm by 3 mm column of 13.times.molecular sieve. Carbon dioxide, propane and propylene can be analyzed using a 2 mm by 3 mm column packed with material sold under the trade name HAYESEP Q® Liquid products (acrylic acid, acrolein, acetic acid and water) can be collected in a cold trap and analyzed using a 2 mm by 3 mm column packed with material sold under the trademark PORAPAK Q®. In all cases, the conversion and selectivity calculations were based on the reaction stoichiometry.

1. Example 1: Preparation of an Exemplary First Catalyst of Formula (I) $Co_aMo_bS_cM_dK_eO_f$ a. Example 1a, Preparation of $CoMoS_2$ (Starting Material for Catalysts)

A solution of $(NH_4)_2MoS_4$ was prepared by dissolving ammonium molybdate tetrahydrate $[(NH_4)_6Mo_7O_{24}4H_2O]$ (15 g) into ammonium sulfide $[(NH_4)_2S/H_2O]$ (106 ml, 20%) with stirring (340-343 K, 1 h). A solution of the cobalt compound was prepared by dissolving cobalt acetate [Co(CH$_3$CO$_2$)$_2$] (10.5 g) in distilled water (200 ml). The two solutions were then added simultaneously drop-wise into a well-stirred solution of aqueous acetic acid solution (30%) at 328 K. The solution was vigorously stirred (1 h, 328 K) and the resultant black solution was filtered and dried at room temperature in a fume cupboard overnight. The resulting slurry was dried at 110° C. for 16 h. The dried sample was heated under nitrogen (1 h, 773 K ramping rate 25K/min), giving a grey-black product, $CoMoS_2$.

b. Example 1b, Preparation of a Supported Catalyst Comprising $CoMoSZn_{0.0065}$ 0.097 g of zinc nitrate dissolved in 6.7 ml of distilled water was added into 10 g of the $CoMoS_2$ until it was in a moldable form between paste and solution state. The resulting slurry was dried at 110° C. for 16 h. The dried sample was heated under nitrogen (1 h, 773 K ramping rate 25 K/min), giving a grey-black product.

This product was then ground and mixed with $K_2CO_3$, bentonite clay and Sterotex® lubricant in a weight ratio of 66 catalyst:10 $K_2CO_3$:20 bentonite:4 Sterotax® and tested under standard conditions described elsewhere herein.

A sample of the catalyst was packed into a tubular reactor, and heated to 580 K while syngas (H2/CO ratio=1:1) was passed over the catalyst at 75 bar, to achieve 92% conversion of the syngas and a 55% selectivity to propane was achieved.

c. Example 1c, Preparation of a Supported Catalyst Comprising $CoMoSTi_{0.0092}$ 0.109 g of Titanium (IV) Oxide Acetylacetonate dissolved in 6.7 ml of acetone was added into 10 g of $CoMoS_2$ until it was in a moldable form between paste and solution state. The resulting slurry was dried at 110° C. for 16 h. This product was then ground and mixed with $K_2CO_3$, bentonite clay and Sterotex® lubricant in a weight ratio of 66/10/20/4 (10% $K_2CO_3$).

A sample of the catalyst was packed into a tubular reactor, and heated to 580 K while syngas ($H_2$/CO ratio=1:1) was passed over the catalyst at 75 bar, to achieve 65% conversion of the syngas and a 17.6% selectivity to propane and a 45.6% selectivity to ethane was achieved

2. Example 2: Preparation of an Exemplary First Catalyst of Formula (II): $Co_{a1}Mn_{b1}Si_{z1}X_{y1}M1_{d1}O_{f1}$ 100 ml of Co and Mn (1 M solutions) were premixed and heated to 80-90° C. in a round bottom flask. 1.2 g of hydrophilic silica having a pH of from 3.7 to 4.7 and a specific surface area of 200 m$^2$/g to 400 m$^2$/g, 0.005 g of lanthanum nitrate, and 0.005 g of ammonium phosphate were dissolved in 20-50 ml of water under continues agitation for 1-2 hrs. The resulting mixture was dried by the incipient wetness method. The resultant solid was added to the Co/Mn solution. Sodium carbonate 1 M solution, preheated at 60-80° C. was added to this Co/Mn solution, which was continuously stirred whilst the temperature was maintained at 80° C. The pH was increased from 2.80 to 9 by addition of carbonate solution.

The resulting precipitate was aged for ½ to 8 hr followed by separating of precipitate from the liquid. The resulting precipitate was washed till sodium free. Material was dried at 110-120° C. for 16 h-24 h and cooked at 300-500° C. for 4-24 h followed by passivation of catalyst precursor with an appropriate media (i.e. S) and thermal treatment. The catalyst precursor was pelleted and sieved to obtain 40-60 mesh sized particles.

3. Example 3: Preparation of an Exemplary First Catalyst of Formula (III): $Co_{a2}Mn_{b2}La_{z2}P_{y2}M2_{d2}O_{f2}$ 100 ml of Co and Mn (1 M solutions) were premixed and heated to 80° C. in a round bottom flask. Ammonium hydroxide solution (5.6 mole/l) preheated at 80° C. was added to the nitrate solution, which was continuously stirred whilst the temperature was maintained at 80° C. The pH was varied from 2.80 to 8.0. A required quantity of lanthanum nitrate (0.017 g) was dissolved in 3.4 ml of distilled water and was added slowly into the of CoMn catalyst precipitate (5 g) followed by addition of 0.0064 g of ammonium phosphate dissolved in 3.4 ml of distilled water. The resulting precipitate was mixed thoroughly to make a homogeneous mixture. Material was dried at 110° C. for 16 h-24 h and calcined at 500-600° C. for 24 h. The calcined catalyst precursor was pelleted and sieved to obtain 0.65-0.85 mm sized particles.

Calcined precursor particles (0.5 g) were loaded into a fixed-bed laboratory reactor. The catalyst precursor was subsequently reduced in situ at 400° C. for 16 h, in a hydrogen atmosphere (GHSV=600 $h^{-1}$).

Temperature was reduced to room temperature and syngas was switched on for reaction. Temperature was increased to 220° C., and pressure was increased to 600 KPa (6 bar) at GHSV=600 $h^{-1}$. A stabilization period of 100 h after initiation of FT synthesis was allowed before mass balance data collection. Propylene and ethylene were identified as significant products of the reaction, 10 to 30% and 10 to 50% by weight respectively.

4. Example 4: Preparation of an Exemplary Second Catalyst of Formula (IV): $Mo_aV_bGa_cPd_dNb_eZ_f$

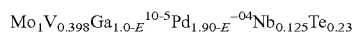

$Mo_1V_{0.398}Ga_{1.0-E}{}^{10-5}Pd_{1.90-E}{}^{-04}Nb_{0.125}Te_{0.23}$

An example of materials suitable as a second catalyst for oxidizing the first product stream to the second product stream, having the composition cited above was prepared by methods described in U.S. Pat. No. 6,160,162 Ammonium metavanadate (Aldrich Chemicals, Assay=99.0%) in the amount of 7.6 grams was added to 80 ml of distilled water and heated to 90° C. with stirring. 3.4 grams of niobium oxide (80% $Nb_2O_5$), 28 grams of oxalic acid, and 28.8 g ammonium paramolybdate tetra hydrate (Aldrich Chemicals A.C.S.-12054-85-2) were added to the vanadate solution to make a gel mixture. The required amount of palladium followed by telluric acid and gallium oxide were added slowly to gel mixture. The gel mixture was stirred vigorously to achieve a homogeneous gel mixture which was then dried slowly to incipient dryness with continuous stirring. The resulting solid was put in a China dish and dried additionally in an oven at 120° C. The dried material was cooled to room temperature and placed in a furnace where the catalyst was calcined at 300 to 600° C. for 4 to 16 hours.

Catalyst evaluation was carried out using 0.40 gram of 38-425 mesh size catalyst samples packed into a stainless steel fixed bed tubular reactor and fed a mixture containing propane:oxygen:nitrogen at a ratio of 71.27:23.75:5 (at a temperature of 305° C., pressure of 15 psig and at space velocity of 1,090 $h^{-1}$). Reaction products were analyzed on-line by gas chromatography. Acrylic acid and acetic acid were products of the reaction.

5. Example 5: Preparation of an Exemplary Supported Second Catalyst of Formula (IV): $Mo_aV_b$-$Ga_cPd_dNb_eZ_f$, Supported on La Modified $SiO_2$

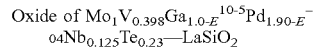

Oxide of $Mo_1V_{0.398}Ga_{1.0-E}{}^{10-5}Pd_{1.90-E}$-$04Nb_{0.125}Te_{0.23}$—$LaSiO_2$ $SiO_2$ was dried overnight at 110-120° C. (5° C./min heating rate). A stock solution of the La precursor was prepared by dissolving 0.2553 g $La(NO_3)_3$ $6H_2O$ in water using a 5.000 ml volumetric flask. The concentration of the solution was 0.05 g/mL on a metal salt basis. To 0.101 g of the $SiO_2$ was added 125 μl of the La stock solution and 375 μl water. The excess liquids were slowly removed for 8-16 hours at 110-120° C. (heating rate 5° C./min) After drying at 120° C. the modified $SiO_2$ was calcined in air at 300-500° C. for 4-10 hours (5° C./min heating rate). The calcined material was finally crushed to a fine powder. 0.45 g $SiO_2$ and 50 mg of the finely ground active phase ($Mo_1V_{0.398}Ga_{1.0E}$-$_{05}Pd_{1.90E-04}Nb_{0.125}Te_{0.23}$) were mixed with 500 μl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation. The acetic acid recycle yield for this reaction was 80% to 95% and the yield for acrylic acid was 70% to 90%.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A method of producing acrylic acid and acetic acid comprising the steps of:
  a) providing a feedstream comprising syngas;
  b) a step consisting of contacting the feedstream with a first catalyst to produce a first product stream comprising C2-C3 olefins and/or C2-C3 paraffins; and
  c) contacting the first product stream with oxygen gas and a second catalyst, thereby producing a second product stream comprising acrylic acid and acetic acid,
    wherein there is no step for separating the components of the first product stream before the first product stream is contacted with the second catalyst,
  wherein the first catalyst is a catalyst composition comprising cobalt; manganese; hydrophilic silica; and at least one element comprising lanthanum, phosphorus, Fe, Zr, or Zn, wherein the relative molar ratios of the elements comprised in said composition are represented by the formula

$Co_{a1}Mn_{b1}Si_{z1}X_{y1}M1_{d1}O_{f1}$, wherein a1 is 1;

wherein b1 is from 0.8 to 1.2;
wherein Si is in the form of a hydrophilic silica;
wherein z1 is from 0.1 to 1;
wherein X is La, P, Fe, Zr, or Zn, or a mixture thereof;
wherein y1 is greater than 0 to 0.005;
wherein M1 is one or more elements selected from the group consisting of alkali metal, alkaline earth metal and transition metal,
wherein d1 is 0 to 0.005; and
wherein f1 is a number determined by the valence requirements of elements of the other elements present in the catalyst.

2. The method of claim 1, wherein the method further comprises separating the acetic acid and the acrylic acid.

3. The method of claim 1, wherein M1 comprises Na, K, Rb, Cs, Mg, Ca, Sr, Ba, Ti, or Zr, or a mixture thereof.

4. The method of claim 1, wherein X is La and P.

5. The method of claim 1, wherein X is one element and is Fe, Zr, or Zn.

6. The method of claim 1, wherein the hydrophilic silica has a specific surface area from 200 $m^2/g$ to 400 $m^2/g$.

7. The method of claim 1, wherein the hydrophilic silica has a pH of 3.7-4.7.

8. The method of claim 1, wherein the first product stream comprises at least 50 mole % C2-C3 olefins and/or C2-C3 paraffins.

9. The method of claim 1, wherein the first product stream does not comprise C1-05 alcohols.

10. The method of claim 1, wherein the second catalyst comprises $$Mo_{a3}V_{b3}Ga_{c3}Pd_{d3}Nb_{e3}Z_{f3},$$

wherein the a3, b3, c3, d3, e3, and f3 are relative molar ratios in the second catalyst,
wherein a3 is 1,
wherein b3 is from 0.01 to 0.9,
wherein c3 is greater than 0 to 0.2,
wherein d3 is from 0.0000001 to 0.2,
wherein e3 is greater than 0 to 0.2,
wherein Z comprises La, Te, Ge, Zn, Si, In, or W, or a mixture thereof, and
wherein f3 is greater than 0 to 0.5.

11. The method of claim 10, wherein Z comprises Te.

12. The method of claim 10, wherein the second catalyst comprises a support material.

13. The method of claim 12, wherein the support material comprises $Al_2O_3$, $SiO_2$, $CeO_2$, $TiO_2$, $ZrO_2$, acetate-$SiO_2$, low surface area $TiO_2$, high surface area $TiO_2$, acetate-$Al_2O_3$, acetate-$ZrO_2$, acetate-$CeO_2$, $AlPO_4$, SiC, silicon-carbide, Mo-carbide, aluminumsilicate, a zeolite, or a molecular sieve, or a mixture thereof.

14. The method of claim 12, wherein the support material is neutral or oxidative.

15. The method of claim 12, wherein the support material comprises additional components $M_s$ and $X_s$,
wherein Ms is a metal comprising B, La, Mn, Sb, Ti, Zr, La, Fe, Cs, Au, or Ce; and
wherein Xs is optionally present and is an alkaline metal comprising Na, K, Mg, or Ca.

16. The method of claim 15, wherein the support material comprises $Al_2O_3$, $SiO_2$, $TiO_2$, $CeO_2$, $AlPO_4$, $ZrO_2$, SiC, Mo-carbide, aluminumsilicate, a zeolite, or a molecular sieve, or a mixture thereof.

17. The method of claim 15, wherein Ms comprises La, Zr, Ce, or Cs.

18. The method of claim 16, wherein Ms comprises La.

19. The method of claim 1, wherein the method consists of steps a)-c).

* * * * *